United States Patent [19]

Mori et al.

[11] Patent Number: 5,254,604
[45] Date of Patent: Oct. 19, 1993

[54] LIGHT POLYMERIZABLE RESIN COMPOSITIONS FOR THE PREPARATION OF CLASP PATTERNS

[75] Inventors: Hiroshi Mori, Chita; Tatsuhiko Takahashi, Nagoya; Akira Hasegawa, Inuyama, all of Japan

[73] Assignee: G-C Toshi Kogyo Corporation, Kasugai, Japan

[21] Appl. No.: 807,655

[22] Filed: Dec. 16, 1991

Related U.S. Application Data

[63] Continuation of Ser. No. 519,316, May 8, 1990, abandoned, which is a continuation-in-part of Ser. No. 348,160, May 8, 1989, abandoned, which is a continuation-in-part of Ser. No. 197,973, May 24, 1988, abandoned.

[30] Foreign Application Priority Data

Jun. 23, 1987 [JP] Japan ................. 62-156101

[51] Int. Cl.⁵ .................................................. G08F 2/46
[52] U.S. Cl. ........................................ 522/95; 430/281; 522/90; 522/908
[58] Field of Search .............. 522/90, 95, 908; 430/281, 286, 287, 288

[56] References Cited

U.S. PATENT DOCUMENTS

| | | | |
|---|---|---|---|
| 4,387,139 | 6/1983 | Herwig et al. | 522/95 |
| 4,668,529 | 5/1987 | Blair. | |
| 4,746,469 | 5/1988 | Yamashita | 522/95 |
| 4,771,084 | 9/1988 | Kubota et al. | 522/908 |

FOREIGN PATENT DOCUMENTS

| | | | |
|---|---|---|---|
| 0014515 | 8/1980 | European Pat. Off. . | |
| 0166009 | 1/1986 | European Pat. Off. | 522/908 |
| 745625 | 2/1956 | United Kingdom . | |

*Primary Examiner*—Jack P. Brammer
*Attorney, Agent, or Firm*—Oblon, Spivak, McClelland, Maier & Neustadt

[57] ABSTRACT

A light-polymerizable resin composition for the preparation of clasp patterns comprises (a) a light-polymerizable compound having at least one ethylenically unsaturated double bond, (b) an organic filler material, (c) a light polymerization initiator and (d) a reducing agent. The light-polymerizable compound is solid at normal temperature, and may be a mono- or polyfunctional acrylate or methacrylate.

9 Claims, 1 Drawing Sheet

LIGHT POLYMERIZABLE RESIN COMPOSITIONS FOR THE PREPARATION OF CLASP PATTERNS

This application is a continuation of application Ser. No. 07/519,316, filed on May 8, 1990, now abandoned, which is a continuation-in-part of 07/348,160, filed May 8, 1989, now abandoned, which is a continuation-in-part of 07/197,973, filed May 24, 1988, now abandoned.

BACKGROUND OF THE INVENTION

1. Field of the Invention

The present invention relates to a light-polymerizable resin composition for making the model or the pattern of a clasp showing a theoretical configuration for providing a retaining force, durability and so on, which is designed to be used to prepare a cast clasp by the lost wax process, said cast clasp being a metallic component or part for gripping (bearing the resistance to lateral movement), retaining (bearing the resistance to attachment or detachment) and supporting (bearing the resistance to an occlusal load) a partial denture, when said partial denture is prepared.

2. Statement of the Prior Art

More than 90% of the direct or indirect retainer used for partial dentures have been clasps. However, not until now has the cast clasp in particular been satisfactory in view of its retaining force, fitness, the form of a given arm etc., since it has been troublesome to prepare.

Referring to the conventional preparation of cast clasps, a gnathic impression is first taken out of the patient's mouth, and a working model is then formed with super-hard gypsum, etc. Subsequently, a tooth portion retained on the working model is surveyed so as to design a clasp that will become a retainer. It is noted that surverying is a work for finding teeth remaining on the working model or the maximum protuberance of an alveolar ridge and, at the same time, to examine relative parallelism, etc., and is very important for the preparation of dentures in view of the purposes of the work which include the determination of the direction of denture attachment/detachment, the determination of the tooth to be retained, the indication of the region to be blocked out, the measurement of the amount to be undercut and the determination of the position of a clasp.

The important factors that govern the retaining force of the clasp include, by way of example, the length, thickness and sectional shape of a clasp arm, the Young's modulus of the alloy used, the present amount of the undercut and the curvature of the surface of the tooth retained. When preparing a cast clasp making use of a paraffinic wax pattern, the retaining force of the clasp may be controlled by the selection of the available amount to be undercut and the thickness and varied sectional shape of the pattern, and the clasp should be designed corresponding to the parodontium state of the tooth retained at the time of surveying or denture designing.

When design and blocking-out is completed for a working model, then the retained tooth portion blocked out according to the design for making the wax pattern of the clasp is again subjected to impression taking (double impression taking) to substitute a modeling investment for the working model. Then, while taking into account the precise control of the retaining force of the clasp, the clasp pattern of paraffinic wax is bent by fingers, and is put on the modeling investment with a bonding agent to form the rest and leg portions and provide a sprue. Next, the modeling investment is entirely invested in a casting investment without removing therefrom the clasp pattern of paraffinic base wax, followed by curing of the investment. Afterwards, the clasp pattern of paraffinic wax is heated and incinerated in a furnace. A molten metal is cast in the resulting die of the clasp pattern, and is cooled and subjected to indexing polishing to complete the clasp. Hereinafter, this method will be referred to as the entire-model-investing method.

The aforesaid method for cast clasp making involves the following problems, since paraffinic wax is used as the material for clasp pattern making.

(1) Paraffinic wax is entirely free from elastic deformation and undergoes plastic deformation. It is thus impossible to remove it from the undercut of the tooth retained on the working model through the maximum protuberance thereof.

Forcible removal of the wax causes it to deform so permanently that any accurate fit is not achievable. For that reason, it is impossible to make any precise clasp having a controlled retaining force. Required to this end is the so-called entire-model-investing method; it is essentially required that the working model be subjected to double impression taking to substitute a modeling investment therefor, and that a clasp pattern be formed on the modeling investment, which is then entirely invested in a casting investment. This method is troublesome and timeconsuming and gives rise to an increase in the material cost.

(2) An exclusive bonding agent has to be always used for the clasp pattern of paraffinic wax, since it shows no adhesion to gypsum. Thus, it is impossible to obtain any clasp showing a good fit, since the resulting clasp exhibits an error of about 50 $\mu$m in the thickness of the adhesive layer.

(3) The clasp pattern of paraffinic wax is pressed and bonded to the modeling investment by fingers with the use of a bonding agent. At that time, however, the particles of the investment peel off due to its low strength, so that the form and surface nature of the tooth retained degrades. The peeling-off investment particles are also deposited onto the clasp pattern of paraffinic wax, thus making it impossible to obtain any cast clasp excelling in surface nature.

(4) The clasp pattern of paraffinic wax is a polymer having a high crystallization and a low molecular weight, and is of a substance which has a glass transition temperature Tg very close to a melting point Tm, but has no glass transistion point as is the case with a metal. Hence, when the wax is incinerated by heating, too high a heating rate causes the molten wax to boil and vaporize into a gas, which in turn expands, and rapidly pressurize the investment with the result that it may crack or roughens on its inner surface.

SUMMARY OF THE INVENTION

In order to solve these problems, the present inventors have now developed a clasp pattern of a new material for paraffinic wax.

As a result of intensive studies made to solve the problems as mentioned above, the present inventors have now successfully developed a light-polymerizable resin composition that is a new substitute for the clasp pattern of paraffinic wax. Reference will first be made to the means for solving the problems as mentioned above.

(1) The present invention does not rely on the so-called entire-model-investing method wherein an impression is again taken out of the working model to substitute the modeling investment therefor for clasp pattern making, and the modeling investment is entirely invested in the casting investment. Rather, the present invention relies upon the method wherein a clasp pattern comprising the light-polymerizable resin composition according to the present invention is bonded and formed on a working model for visible-light polymerization, and the thus polymerized clasp pattern is removed from the working model, and is invested in a casting investment for casting. Required to this end is a material which is rich in plasticity and freely deformable at the stage of bonding and forming the clasp pattern on the working model, as is the case with the conventional wax, and is cured immediately upon exposed to active energy rays such as visible rays or ultraviolet rays to provide a cured body which does not deform at all, even after removed from the working model.

The light-polymerizable resin composition of the present invention meets such requirements, and has the properties of being removed from an undercut portion of a site to which a clasp is attached through a maximum protuberance with a maximum deformation of about 0.5 mm but without fracturing, and being precisely restored to the original form. When preparing a cast clasp with the use of the light-polymerizable clasp pattern of this material, the steps of taking an impression of a tooth portion retained on the working model and of substituting the modeling investment for the working model can be omitted, so that the length of time of about 8 hours so far required can be nearly halved. In addition, the material costs for the precision and modeling investments heretofore used can be cut down.

(2) Unlike paraffinic wax, the material of the composition obtained according to the present invention is so compatible with respect to gypsum that it can suitably adhere to gypsum in the absence of any adhesives, and be easily removed therefrom after curing. It is thus possible to prevent unsatisfactory fits due to the thickness of the adhesive layer and, hence, make a cast clasp of improved fit accuracy.

(3) The material of the composition obtained according to the present invention can suitably adhere to an investment without using any adhesives, and has no adverse influence upon the form and surface nature of the retained tooth, since it is very unlikely that the investment may peel off due to pressure contact by fingers. In addition, since there is no fear that investment particles are deposited onto the clasp pattern, it is possible to make a cast clasp of improved surface nature.

(4) The composition obtained in accordance with the present invention is a crystalline high-molecular material comprising a crystalline moiety (in which the molecules are orientated) and an amorphous moiety (in which the molecules are not orientated) and having a glass transition point Tg in the vicinity of 90° C. This material softens gradually until a temperature is nearly reached at which the cured mass, now a thermosetting resin, decomposes; then carbonizes; and is finally converted to carbon dioxide and water for incineration. It is thus possible to obtain a cast clasp having a satisfactory cast surface, which is free from boiling expansion, cracking of the investment due to sharp pressurization and roughening of the inner face of the investment, as found in the conventional wax pattern of paraffinic wax.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1A:
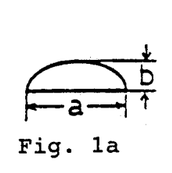
FIGS. 1a through 1d are end views of the clasps described in Table 1.
Figure 1B:
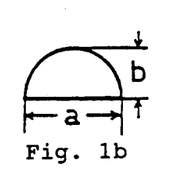
Figure 1C:
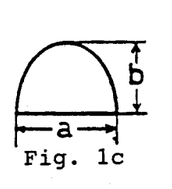
Figure 1D:
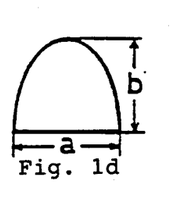
Figures 2A, 2B:
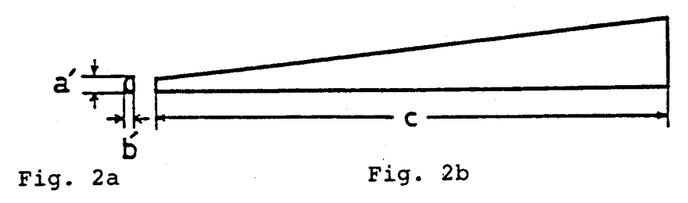
FIG. 2a is an end view of one end of the clasp described in Table 1.
FIG. 2b is a side view of the clasp described in Table 1.
Figure 2C:
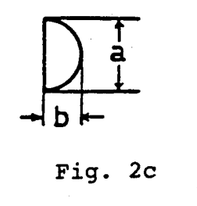
FIG. 2c is an end view of the other end of the clasp described in Table 1.

Of the light-polymerizable compounds used in the present invention, which are solid at normal temperature and have at least one ethylenically unsaturated double bond, examples of monofunctional methacrylates include methoxy polyethylene glycol 1000 methacrylate; examples of monofunctional acrylates, methoxy polyethylene glycol 1000 acrylate; examples of polyfunctional methacrylates, the products of reaction between diisocyanate methylbenzene and 2-hydroxyethyl methacrylate (manufactured by Negami Kogyo, Co., Ltd. and available in the brand name of Art Resin SH-100), diisocyanate methylcyclohexane and 2-hydroxyethyl methacrylate (manufactured by Negami Kogyo, Co., Ltd. and available in the brand name of Art Resin SH-200), isophorone diisocyanate and 2-hydroxyethyl methacrylate (manufactured by Negami Kogyo, Co., Ltd. and available in the brand name of Art Resin SH-300), hexamethylene diisocyanate and 2-hydroxyethyl methacrylate (manufactured by Negami Kogyo, Co., Ltd. and available in the brand name of Art Resin SH-400), hexamethylene diisocyanate and 2-hydroxypropyl methacrylate (manufactured by Negami Kogyo, Co., Ltd. and available in the brand name of Art Resin SH-420), hexamethylene diisocyanate and 3-chloro-2-hydroxypropyl methacrylate (manufactured by Negani Kogyo, Co., Ltd. and available in the brand name of Art Resin SH-440) and methylene-bis(4-cyclohexyl isocyanate) and 2-hydroethyl methacrylate (manufactured by Negami Kogyo, Co., Ltd. and available in the brand name of Art Resin SH-600), tris(methacryloxyethyl)isocyanate and polyethylene glycol 1000 dimethacrylate; and examples of polyfunctional acrylates, tris(acryloxyethyl)isocyanate, pentaerythritol tetraacrylate, pentaerythritol triacrylate or suitably a polyfunctional acrylate having the following structural formula:

wherein $R_1$, $R_2$ and $R_3$ each are an alkyl group (manufactured by Shin-Nakamura Kagaku Co., Ltd. and available in the brand name of U-108A).

As the organic fillers used in the present invention, use may be made of, alone or in combination, polyolefin powders (e.g., polyethylene and polypropylene powders etc.), polyacrylic ester powders (e.g., methyl and ethyl polyacrylates etc.), polymethacrylic ester powders (e.g., methyl and ethyl polymethacrylates etc.), methacrylic ester copolymer powders (e.g., a copolymer of methyl polymethacrylate and ethyl polymethacrylate etc.), acrylic ester copolymer powders (e.g., a copolymer of methyl polyacrylate and ethyl polyacrylate etc.), crosslinked type methacrylic ester powders (e.g., methyl polymethacrylate crosslinked with trimethylolpropane trimethacrylate etc.), styrene-butadiene copolymer powders, acrylonitrile-styrene copolymer powders, acrylonitrile-styrene-butadiene copolymer powders, nylon powders etc. The amount of the organic fillers added should preferably be 0.1 to 90 parts by weight with respect to 100 parts by weight of the light-polymerizable compounds.

As the light-polymerization initiators used, effective use may be made of α-diketone compounds, ketal compounds, anthraquinone compounds, thioxanthon compounds and benzoin alkyl ether compounds. More definitely, effective as the α-diketone compounds are d,l-camphor quinone, benzyl, diacetyl, acenaphthene quinone and 9,10-phenanthrene quinone. Among others, particular preference is given to d,l-camphor quinone and benzyl. As the ketal compounds, effective use may be made of benzyl dimethyl ketal, benzyl diethyl ketal, benzyl dipropyl ketal, benzyl-di(β-phenylethyl)ketal, benzyl di-(2-methoxyethyl)ketal, benzyl di-(2-ethoxyethyl)ketal, benzyl di-(2-methoxyethoxyethyl)ketal, benzyl di-(2-ethoxyethoxethyl)ketal, 4,4'-dimethylbenzyl dimethyl ketal, 2,2'-dimethoxybenzyl diethyl ketal, 4,4'-dichlorobenzyl-diethyl ketal and 4,4'-dichlorobenzyl dipropyl ketal, by way of example. Among others, particular preference is given to benzyl dimethyl ketal, benzyl diethyl ketal, benzyl di-(2-methoxyethyl)ketal and 4,4'-dimethylbenzyl dimethyl ketal.

As the anthraquinone compounds, effective use may be made of anthraquinone, 1-chloroanthraquinone, 2-chloroanthraquinone, 1,2-benzanthraquinone, 1-hydroxyanthraquinone, 1-methylanthraquinone, 2-ethylanthraquinone and 1-bromoanthraquinone, by way of example. Among others, particular preference is given to anthraquinone, 1-chloroanthraquinone and 1,2-benzanthraquinone. As the thioxanthon compounds, effective use may be made of thioxanthone, 2-chlorothioxanthon, 2-isopropylthioxanthon, 2-nitrothioxanthon, 2-methylthioxanthon, 2,4-dimethyloxanthon, 2,4-diethylthioxanthon, 2,4-diIsopropylthioxanthon, 2-chloro-7-trifluorormethylthioxanthon, thioxanthon-10,10-dioxide and thixanthon-10-oxide, by way of example. Among others, particular preference is given to thioxanthon, 2-chlorothioxanthon, 2,4-dimethylxanthon, 2,4-diethylthioxanthon and 2,4-diisopropylthioxanthon.

As the benzoin alkyl ether compounds, effective use may be made of benzoin methyl ether, benzoin ethyl ether, benzoin isopropyl ether, benzoin-n-butyl ether and benzoin butyl ether, by way of example. Among others, particular preference is given to benzoin butyl ether.

The light-polymerization initiators as mentioned above may be used alone or in combination. Preferably, the amount of the light-polymerization initiators incorporated should be 0.001 to 5 parts by weight with respect to 100 parts by weight of the light-polymerizable compounds which are solid at normal temperature and have at least one ethylenically unsaturated double bond. In an amount of less than 0.001 part by weight, the compositions are so poor in reactivity that the depth of curing time is increased with the depth of curing being limited, on the one hand and in an amount exceeding 5 parts by weight excessive catalysts act as a plasticizer to decrease the strength of the cured products on the other.

According to the present invention, the reducing agents used should be capable of reducing a photosensitizer while excited, but incapable of reducing a photosensitizer while not excited by active energy rays. The reducing agents may be primary, secondary and tertiary amine, as expressed by:

wherein at most two of R, R' and R" may be a hydrogen atom, or at least one of R, R' and R" may be a different or identical hydrocarbon group. The hydrocarbon group may be an alkyl, cycloalkyl, hydroxyalkyl or aralkyl group. Preferably, the groups R, R' and R" should be an alkyl group having one to ten carbon atoms.

Suitable examples of the reducing agents, wherein at least one of the groups R, R' and R" is a hydrocarbon group, include propylamine, n-butylamine, pentylamine, hexylamine, dimethylamine, diethylamine, dipropylanine, di-n-butylamine, dipentylamine, 2-dimethylaminoethanol, trimethylamine, triethylamine, tripropylamine, tri-n-butylamine, tripentylamine, dimethylaminoethyl methacrylate, diethylaminoethyl methacrylate, triethanolamine and long-chain aliphatic amities.

Examples of the reducing agents containing aromatic groups include N,N'-dimethylaniline, N,N'-dimethyl-p-toluidine, p-tolyldiethanoiamine, m-tolyldiethanolamine, N-methyldiphenylamine, ethyl 2-dimethylaninobenzoate, ethyl 4-dimethylaminobenzoate, methyl 4-dimethylaminobenzoate, butyl 4-dimethylaminobenzoate, 2-ethylhexyl 4-dimethylaminobenzoate and isoamyl 4-dimethylaminobenzoate.

Use may also be made of diamines having the following structural formula:

wherein n is an integer of 2 or more, and R, R', R", and R"' may be different or identical and each stand for a hydrogen atom or a hydrocarbon group, inter alia, an alkyl group. Examples of such diamine reducing agents include ethylenediamine, trimethyldiamine, tetramethylenediamine, pentamethylenediamine or hexamethylenediamine, or their N-hydrocarbon group derivatives, inter alia, their alkyl group derivatives.

Examples of the reducing agents, in which an element N forms a part of their ring systems, include piperidine and its N-hydrocarbon group derivatives. Other reducing agents may include triarylamines, allylthioureas, aromatic sulfites, 5-alkyl or 5-aryl barbituric acid, by way of example.

Of these reducing agents, preference is given to dimethylaminoethyl methacrylate, triethanolamine, methyl 4-dimethylaminobenzoate and ethyl 4-dimethylaminobenzoate.

Preferably, the amount of these reducing agents added should be 0.01 to 10 parts by weight with respect to 100 parts by weight of the light-polymerizable compounds having at least one ethylenically unsaturated double bond. When these reducing agents are added in an amount of less than 0.01 part by weight, the compositions are so poor in reactivity that the depth of curing time is increased, while the depth of curing is limited on the one hand. When they are added in an amount exceeding 10 parts by weight the compositions degrade in storage stability so that a time allowed for dental manipulation by usual indoor illumination is very limited on the other.

It is desired that the light-polymerizable compositions for clasp patterns be pre-for-med to a shape suitable for clasp pattern making, as illustrated in the following Table I by way of example.

TABLE 1

| Form of Section | No. 1 | No. 2 | No. 3 | No. 4 |
|---|---|---|---|---|
| a:b | 10:3 | 10:5 | 10:7 | 10:9 |
| a | 3.79 ± 0.4 | 3.05 ± 0.4 | 2.48 ± 0.4 | 2.14 ± 0.4 |
| b | 1.20 ± 0.4 | 1.67 ± 0.4 | 1.78 ± 0.4 | 1.97 ± 0.4 |
| a' | 1.21 ± 0.15 | 0.94 ± 0.15 | 0.81 ± 0.15 | 0.71 ± 0.15 |
| b' | 0.42 ± 0.15 | 0.53 ± 0.15 | 0.62 ± 0.15 | 0.66 ± 0.15 |
| c | 25.00 ± 0.2 | 25.00 ± 0.2 | 25.00 ± 0.2 | 25.00 ± 0.2 |

[Unit:mm]

The shapes, as illustrated in Table I for the purpose of illustration alone, are important in controlling a retaining force occurring at the time of partial denture attachment/detachment or occlusion.

EXAMPLES

In the examples and comparative examples, the following compositions were prepared to carry out Experiments 1 to 8, whereby the effect of the present invention was ascertained; however, such examples are intended to illustrate the invention and are not to be construed to limit the scope of the invention.

Examples 1 to 26

The compositions prepared are set out in Table 2.

Example 27

The compositions prepared are set out in Table 3.

Comparative Examples 1 to 6

These examples were carried out in order to define the examples according to the present invention. The compositions prepared were set out in Table 2.

Comparative Example 7

In the light-polymerizable compositions for clasp patterns according to the present invention, an inorganic filler was used for the organic filler. The composition prepared was shown in Table 2.

Comparative Example 8

Use was made of a clasp pattern of commercially available paraffinic wax (manufactured by G-C Dental Industrial Corp. and available in the brand-name of GC Clasp Pattern).

Examples 1 to 27 and Comparative Examples 1 to 8 were conducted in the following manner.

The light-polymerizable compound, which is solid at normal temperature and has at least one ethylenically unsaturated double bond, is first heated at a temperature of higher than its melting point (about 60° to 80° C.) into a melt. Suitable amounts of the light polymerization initiator and reducing agent are then added to and stirred with the melt until they are uniformly dissolved. The predetermined amount of the thus completely dissolved product is put in a mortar controllable to a temperature of about 80° C., and the organic filler is slowly added to and stirred with it in an amount corresponding to the aforesaid amount. A pasty product, in which the organic filler is uniformly mixed and dispersed, is defoamed in a vacuum defoaming machine capable of heating it. The thus defoamed paste is cooled down to room temperature, and is press-molded in a mold designed for the shapes shown in Table 1, from which the molding is then removed. It is noted that all the steps are carried out at 100 V, 60 W and 500 Lx or less under a red lamp.

The effect of the present invention was then ascertained by Experiments 1 to 8, as shown in Tables 2 and 3.

EXPERIMENT 1

Manipulatability Before Curing

The compositions should be free from stickiness and rich in flexibility.

EXPERIMENT 2

Bending Strength After Curing [I.S.O. 4049(25×2×2 mm)]

(In the case of the use of the ketal and benzoin alkyl ether initiators, the irradiating time is 1 minute on each side, that is total 2 minutes on its both sides with GC Labolight LV-I—brand name—manufactured by G-C Dental Industrial Corp. at 1 mm/min. C.H.S. except compositions that were irradiated for 20 minutes with Permacure UC-I—brand name—manufactured by G-C Dental Industrial Corp.)

It does not follow that the values of the data are bigger the better but that the data, if about 200 kg/cm² or more, will suffice practically.

Experiment 3

Cinders (incinerated at 600° C. for 1 hour in an autofurnace)

The amount of cinders should be reduced to zero.

EXPERIMENT 4

Curing Time (The compositions which contain the ketal and benzoin alkyl ether initiators were irradiated with GC Labolight LV-I—brand name—manufactured by G-C Dental Industrial Corp. to determine the degree of curing by Vicat indentation except the composition that were irradiated with GC Permacure UC-I—brand name—manufactured by G-C Dental Industrial Corp. to determine the degree of curing every 5 seconds by Vicat indentation.) A curing time of 30 seconds to 90 seconds indicates that the compositions are easy to manipulate. A curing time below 30 seconds sometimes implies that a time allowed for manipulation is short, while a curing time exceeding 90 seconds indicates that any sharp curing by light polymerization cannot be utilized.

EXPERIMENT 5

Curing Depth (The compositions which contain the ketal and benzoin alkyl ether initiators are irradiated for 40 seconds with GC Light VL-I—brand name—manufactured by G-C Dental Industrial Corp., and the uncured portions were washed with ethyl alcohol and wiped out by gauze except the compositions that were irradiated for 20 minutes with GC Permacure UC-I—brand name—manufactured by G-C Dental Industrial Corp., and the uncured portions were washed with ethyl alcohol and wiped out by gauze.)

Since the thickest No. 1 clasp pattern is 3.79 mm in thickness, a curing depth should exceed that figure. Depending upon cases, it is very likely that the rest or leg portion may be about 4 mm in thickness. It is thus desired that a curing depth exceeds 4 mm.

EXPERIMENT 6

Time for Clasp Making

Length of time required from surveying of working models to polishing of castings.

EXPERIMENT 7

Need for Adhesives

For instance, whether the preform bond manufactured by G-C Dental Industrial Corp., Ltd is needed or not.

EXPERIMENT 8

State of Cast Surface

Whether surface roughening is found or not.

In Examples 1 to 9 and those 11 to 16 as well as Examples 18 to 26, methyl polymethacrylate powders were incorporated into the light-polymerizable compounds which are solid at normal temperature and have at least one ethylenically unsaturated double bond; in Example 10, polypropylene powders were mixed; and in Example 17, styrene/butadiene copolymer powders were added. In Examples 11, 12, 18, 19 and 20, the amount of methyl polymethacrylate powders were varied; no appreciable influence upon physical properties was found within this range.

The light polymerization initiators used in Examples 1, 5 to 22 and 24 to 26 are d,l-camphor quinone, and those used in Examples 2, 3, 4 and 23 are respectively 1,2-benzanthraquinone, thioxanthon, benzoin isobutyl ether and benzyl dimethyl ketal. Of these initiators, 1,2-benzanthraquinone produces a sufficient effect in a slight amount. The reducing agents used in Examples 1 to 4 and 6 to 26 are dimethylaminoethyl methacrylate, and the reducing agent used in Example 5 is methyl 4-dimethylaminobenzoate. In Examples 13 and 25, the amount of the light polymerization initiator d,l-camphor quinone was decreased, and in Example 14, it was increased. A smaller or larger amount of d,l-camphor quinone tends to increase or decrease the depth of curing time; however, no practical problem arises as long as it is within the scope as defined in the appended claims. In Examples 15 and 26, the amount of the reducing agent, dimethylaminoethyl methacrylate added, was reduced, and in Example 16, it was increased. A smaller or larger amount of dimethylaminoethyl methacrylate added tends to increase or decrease the depth of curing time; however, no practical problem arises as long as it is within the scope as defined in the appended claims.

In Examples 1 to 5, 10 to 20, 23, 25 and 26, the polyfunctional acrylate was used as the light-polymerizable compounds which were solid at normal temperature and had at least one ethylenically unsaturated double bond, and in Examples 6 and 7, the polyfunctional methacrylate was used. In Examples 8, 9 and 24, a mixture of the polyfunctional acrylate and methacrylate was used. In Examples 21 and 22, the monofunctional methacrylate and acrylate were respectively used.

Example 27 is one of the embodiments of the present invention wherein two kinds of the polyfunctional methacrylate are mixed for use as a solid compound light-polymerizable in normal temperature containing at least one ethylenically unsaturated double bond and the use is made of methyl polymethacrylate powder crosslinked with trimethylolpropane trimethacrylate as a filler. The use of this filler makes it possible to obtain an improved cast surface in particular. Further, the depth of curing is about twice as deep compared with other embodiments which shows well-made polymerization.

In Comparative Examples 1 and 4, the amount of the organic filler material, methyl polymethacrylate powders, departed from the preferable range. When that amount is smaller as in Comparative Example 1, stickiness in manipulatability appears, and when that amount is larger as in Comparative Example 4, the composition loses flexibility and becomes fragile. Comparative Examples 2 and 3, wherein the amounts of the initiator d,l-camphor quinone and the reducing agent dimethylaminoethyl methacrylate are smaller than the lower limits of the preferable ranges, indicate that insufficient polymerization gives rise to a lowering of bending strength, increases in the depth of curing time and decreases in the depth of curing. Comparative Examples 5 and 6, wherein the amounts of d,l-camphor quinone and dimethylaminoethyl methacrylate added were larger than the upper limits of the preferable ranges, reveal that a time allowed for manipulation is short due to too rapid curing, and that a larger amount of d,l-camphor quinone gives rise to a lowering of bending strength. This is considered to be due to the fact that excess catalyst acts as a plasticizer, resulting in a lowering of bending strength. Comparative Example 7, wherein an inorganic filler was added as the filler material, bears resemblance to the composition of a conventional composite resin. Since the filler is inorganic, the amount of cinders is not reduced to zero. Thus, this composition does not function at all to make clasps.

In Comparative Example 8, a conventional clasp pattern of paraffinic wax was used, that is, the GC clasp pattern manufactured by G-C Dental Industrial Corp. was used. About 8 hours were required for clasp making due to the use of the entire-model-investing method wherein the modeling investment was substituted for the working model for the next surveying and casting. This figure is nearly twice the length of time needed in the case of the light-polymerizable composition for clasp patterns according to the present invention. Further, the bonding agent (e.g., Preform Bond manufactured by G-C Dental Industrial Corp.) for bonding to the modeling investment is always required in order to use the clasp pattern of paraffinic wax. Still further, slight adverse influences are produced on the state of a cast surface depending upon the conditions for the incineration of wax, the type of investments and so on.

| | A light-polymerizable compound having at least one ethylenically unsaturated double bond | | | | | Filler | | | | |
|---|---|---|---|---|---|---|---|---|---|---|
| | Monofunctional | | Polyfunctional | | | Organic Filler | | | Inorganic Filler | |
| | Methacrylate | Acrylate | Methacrylate | | Acrylate | Methyl | Poly- | Styrene | Fine Glass | Colloidal |
| | Methoxy Polyethylene Glycol 1000 Methacrylate (Parts by weight) | Methoxy Polyethylene Glycol 1000 Acrylate (Parts by weight) | Art Resin SH-100 (Negami Kogyo Co.) (Parts by weight) | Art Resin SH-600 (Negami Kogyo Co.) (Parts by weight) | U-108A (Shin-Nakamura Kagaku Co.) (Parts by weight) | Poly-methacrylate Powder (Parts by weight) | propylene Powder (Parts by weight) | Butadiene Copolymer Powder (Parts by weight) | Powder (Processed with Silane Coupling) (Parts by weight) | Silica (Processed with Silane Coupling) (Parts by weight) |
| Example 1 | | | | | 100 | 60 | | | | |
| Example 2 | | | | | 100 | 60 | | | | |
| Example 3 | | | | | 100 | 60 | | | | |
| Example 4 | | | | | 100 | 60 | | | | |
| Example 5 | | | | | 100 | 60 | | | | |
| Example 6 | | | 100 | | | 50 | | | | |
| Example 7 | | | | 100 | | 50 | | | | |
| Example 8 | | | 40 | | 60 | 60 | | | | |
| Example 9 | | | | 40 | 60 | 60 | | | | |
| Example 10 | | | | | 100 | | 60 | | | |
| Example 11 | | | | | 100 | 5 | | | | |
| Example 12 | | | | | 100 | 80 | | | | |
| Example 13 | | | | | 100 | 60 | | | | |
| Example 14 | | | | | 100 | 60 | | | | |
| Example 15 | | | | | 100 | 60 | | | | |
| Example 16 | | | | | 100 | 60 | | | | |
| Example 17 | | | | | 100 | | | 60 | | |
| Example 18 | | | | | 100 | 40 | | | | |
| Example 19 | | | | | 100 | 30 | | | | |
| Example 20 | | | | | 100 | 0.5 | | | | |
| Example 21 | 100 | | | | | 60 | | | | |
| Example 22 | | 100 | | | | 60 | | | | |
| Example 23 | | | | | 100 | 60 | | | | |
| Example 24 | | | 20 | 20 | 60 | 60 | | | | |
| Example 25 | | | | | 100 | 60 | | | | |
| Example 26 | | | | | 100 | 60 | | | | |
| Comparative Example 1 | | | | | 100 | 0.05 | | | | |
| Comparative Example 2 | | | | | 100 | 60 | | | | |
| Comparative Example 3 | | | | | 100 | 60 | | | | |
| Comparative Example 4 | | | | | 100 | 95 | | | | |
| Comparative Example 5 | | | | | 100 | 60 | | | | |
| Comparative Example 6 | | | | | 100 | 60 | | | | |
| Comparative Example 7 | | | | | 100 | | | | 350 | 50 |
| Comparative Example 8 | | | | | 100 | | | | | |

(Example wherein GC clasp pattern of the paraffinic wax manufactured by G-C Dental Industrial Corp. was used.

| | Light-Polymerization Initiator | | | | | Reducing Agent | | Polymerization |
|---|---|---|---|---|---|---|---|---|
| | α-Diketone | Ketal | Antraquinone | Thioxanthon | Benzoin Alkyl Ether | | | |
| | Compound d,l-Camphor-quinone (Parts by weight) | Compound Benzyl Dimethyl Ketal (Parts by weight) | Compound 1,2-Benz-anthra-quinone (Parts by weight) | Compound Thioxan-thon (Parts by weight) | Compound Benzoin Isobutyl Ether (Parts by weight) | Dimethyl aminoethyl Methacrylate (Parts by weight) | Ethyl 4-Dimethyl-amino-benzoate (Parts by weight) | Inhibitor Butyl Hydroxy Toluene (Parts by weight) |
| Example 1 | 0.5 | | | | | 0.5 | | 0.03 |
| Example 2 | | 0.02 | | | | 0.5 | | 0.03 |
| Example 3 | | | 0.5 | | | 0.5 | | 0.03 |
| Example 4 | | | | | 0.5 | 0.5 | | 0.03 |
| Example 5 | 0.5 | | | | | | 0.5 | 0.03 |

-continued

|  | col A | col B | col C | col D |
|---|---|---|---|---|
| Example 6 | 0.5 |  | 0.5 | 0.03 |
| Example 7 | 0.5 |  | 0.5 | 0.03 |
| Example 8 | 0.5 |  | 0.5 | 0.03 |
| Example 9 | 0.5 |  | 0.5 | 0.03 |
| Example 10 | 0.5 |  | 0.5 | 0.03 |
| Example 11 | 0.5 |  | 0.5 | 0.03 |
| Example 12 | 0.5 |  | 0.5 | 0.03 |
| Example 13 | 0.01 |  | 0.5 | 0.03 |
| Example 14 | 4.5 |  | 0.5 | 0.03 |
| Example 15 | 0.5 |  | 0.1 | 0.03 |
| Example 16 | 0.5 |  | 9 | 0.03 |
| Example 17 | 0.5 |  | 0.5 | 0.03 |
| Example 18 | 0.5 |  | 0.5 | 0.03 |
| Example 19 | 0.5 |  | 0.5 | 0.03 |
| Example 20 | 0.5 |  | 0.5 | 0.03 |
| Example 21 | 0.5 |  | 0.5 | 0.03 |
| Example 22 | 0.5 |  | 0.5 | 0.03 |
| Example 23 |  | 0.5 | 0.5 | 0.03 |
| Example 24 | 0.5 |  | 0.5 | 0.03 |
| Example 25 | 0.005 |  | 0.5 | 0.03 |
| Example 26 | 0.5 |  | 0.5 | 0.03 |
| Comparative Example 1 | 0.5 |  | 0.5 | 0.03 |
| Comparative Example 2 | 0.0005 |  | 0.5 | 0.03 |
| Comparative Example 3 | 0.5 |  | 0.005 | 0.03 |
| Comparative Example 4 | 0.5 |  | 0.5 | 0.03 |
| Comparative Example 5 | 6 |  | 0.5 | 0.03 |
| Comparative Example 6 | 0.5 |  | 12 | 0.03 |
| Comparative Example 7 | 0.5 |  | 0.5 | 0.03 |
| Comparative Example 8 | (Example wherein GC clasp pattern of the paraffinic wax manufactured by G-C Dental Industrial Corp. was used. | | | |

| | | | | Physical Properties | | | | |
|---|---|---|---|---|---|---|---|---|
|  | Manipulata- bility Before Curing | (NB1) Bending Strength after Curing ( ) Standard Deviation (kg/cm$^2$) | (NB2) Curing Time (Second) | (NB3) Depth of Curing (mm) | Amount of Cinders (In 700° C.) for two hours by Autofurnace (%) | Time for Clasp Making | Necessity of Bonding Agent for Clasp Pattern (GC Preform Bond) | State of Cast Surface (Investment: Cristobalite Micro Metal: Castwell 12 of G-C Industrial Corp. |
| Example 1 | Good | 413 (31) | 50 | 4.68 | 0 | Approx. 4 hours | Not Necessary | Excellent |
| Example 2 | Good | 480 (13) | 35 | 4.82 | 0 | Approx. 4 hours | Not Necessary | Excellent |
| Example 3 | Good | 401 (64) | 45 | 4.53 | 0 | Approx. 4 hours | Not Necessary | Excellent |
| Example 4 | Good | 361 (22) | 45 | 4.66 | 0 | Approx. 4 hours | Not Necessary | Excellent |
| Example 5 | Good | 447 (62) | 45 | 4.79 | 0 | Approx. 4 hours | Not Necessary | Excellent |
| Example 6 | Good | 396 (8) | 50 | 4.63 | 0 | Approx. 4 hours | Not Necessary | Excellent |
| Example 7 | Good | 502 (19) | 50 | 4.49 | 0 | Approx. 4 hours | Not Necessary | Excellent |
| Example 8 | Good | 511 (67) | 45 | 4.28 | 0 | Approx. 4 hours | Not Necessary | Excellent |
| Example 9 | Good | 422 (19) | 45 | 4.72 | 0 | Approx. 4 hours | Not Necessary | Excellent |
| Example 10 | Good | 313 (11) | 45 | 4.38 | 0 | Approx. 4 hours | Not Necessary | Excellent |
| Example 11 | Good | 452 (83) | 40 | 5.01 | 0 | Approx. 4 hours | Not Necessary | Excellent |
| Example 12 | Good | 229 (10) | 55 | 4.03 | 0 | Approx. | Not | Excellent |

-continued

| | Manipulatability Before Curing | (NB1) Bending Strength after Curing ( ) Standard Deviation (kg/cm²) | (NB2) Curing Time (Second) | (NB3) Depth of Curing (mm) | Amount of Cinders (In 700° C.) for two hours by Autofurnace (%) | Time for Clasp Making | Necessity of Bonding Agent for Clasp Pattern (GC Preform Bond) | State of Cast Surface (Investment: Cristobalite Micro Metal: Castwell 12 of G-C Industrial Corp. |
|---|---|---|---|---|---|---|---|---|
| Example 13 | Good | 387 (39) | 60 | 4.11 | 0 | Approx. 4 hours | Not Necessary | Excellent |
| Example 14 | Good | 429 (55) | 30 | 4.89 | 0 | Approx. 4 hours | Not Necessary | Excellent |
| Example 15 | Good | 366 (57) | 70 | 4.01 | 0 | Approx. 4 hours | Not Necessary | Excellent |
| Example 16 | Good | 472 (41) | 35 | 4.88 | 0 | Approx. 4 hours | Not Necessary | Excellent |
| Example 17 | Good | 488 (29) | 40 | 4.22 | 0 | Approx. 4 hours | Not Necessary | Excellent |
| Example 18 | Good | 462 (61) | 45 | 4.21 | 0 | Approx. 4 hours | Not Necessary | Excellent |
| Example 19 | Good | 413 (5) | 45 | 4.68 | 0 | Approx. 4 hours | Not Necessary | Excellent |
| Example 20 | Good | 450 (18) | 50 | 4.99 | 0 | Approx. 4 hours | Not Necessary | Excellent |
| Example 21 | Good | 296 (30) | 50 | 4.22 | 0 | Approx. 4 hours | Not Necessary | Excellent |
| Example 22 | Good | 280 (13) | 50 | 4.18 | 0 | Approx. 4 hours | Not Necessary | Excellent |
| Example 23 | Good | 434 (24) | 40 | 4.62 | 0 | Approx. 4 hours | Not Necessary | Excellent |
| Example 24 | Good | 496 (61) | 40 | 4.83 | 0 | Approx. 4 hours | Not Necessary | Excellent |
| Example 25 | Good | 409 (66) | 75 | 4.08 | 0 | Approx. 4 hours | Not Necessary | Excellent |
| Example 26 | Good | 421 (33) | 80 | 4.16 | 0 | Approx. 4 hours | Not Necessary | Excellent |
| Comparative Example 1 | Sticky | 459 (39) | 40 | 5.66 | 0 | Approx. 4 hours | Not Necessary | Excellent |
| Comparative Example 2 | Good | 144 (4) | 160 | 1.21 | 0 | Approx. 4 hours | Not Necessary | Excellent |
| Comparative Example 3 | Good | 208 (36) | 245 | 2.09 | 0 | Approx. 4 hours | Not Necessary | Excellent |
| Comparative Example 4 | Fragile | Not Measurable | Not Measurable | Not Measurable | 0 | Not Possible to Manufacture Clasp | | |
| Comparative Example 5 | Good | 201 (28) | 25 | 4.81 | 0 | Approx. 4 hours | Not Necessary | Excellent |
| Comparative Example 6 | Good | 414 (19) | 20 | 5.03 | 0 | Approx. 4 hours | Not Necessary | Excellent |
| Comparative Example 7 | Form not maintained | 1038 (69) | 45 | 5.37 | 78.8 | Not Possible to Manufacture Clasp | | |
| Comparative Example 8 | Good | Not Measurable | Not Measurable | Not Measurable | 0 | Approx. 8 hours | Necessary | Good |

(NB1)
Test material was prepared by irradiating the material with GC Permacure UC-I for twenty minutes in the case of light-polymerization initiator of ketal and of benzoin alkyl ether were used. For others, test material was prepared by irradiating the materials on its one side with GC Labolight LV-I each for one minute in preparing the test material.
(NB2)
In the case of the use being made of light-polymerization initiator of ketal and of benzoin alkyl ether, curing is measured by means of irradiating the material with GC Permacure UC-I followed by Vicat indentation at five second interval. For others, measurement was taken similarly by irradiation with GC Labolight LV-I.
(NB3)
Twenty minute irradiation with GC Permacure UC-I effected to light-polymerization initiator of ketal and of benzoin alkyl ether, and for others, GC Light VL-I was irradiated for forty seconds.

TABLE 3

| | A light-polymerizable compound having at least on ethylenically unsaturated double bond Polyfunctional Methacrylate | | Filler Organic Filler Methyl Polymethacrylate | Light-Polymerization Initiator | Reducing Agent Dimethyl- | Polymerization Initiator |
|---|---|---|---|---|---|---|
| | Art Resin SH-100 (Nogami Kogyo Co.) (Parts by Weight) | U-108 (Shin-Nakamura Kagaku Co.) (Parts by Weight) | Powder Crosslinked with Trimethylolpropane Trimethacrylate (Parts by Weight) | α-Diketone d,l-Camphor-quinone (Parts by Weight) | amino Ethyl Methacrylate (Parts by Weight) | Butyl Hydroxy Toluen (Parts by Weight) |
| Example 27 | 50 | 50 | 80 | 1.0 | 1.0 | 0.03 |

| Physical Properties | | |
|---|---|---|
| (NB1) | | State of |

TABLE 3-continued

| | Manipulat- ability Before Curing | Bending Strength After Curing ( ) Standard Deviation (kg/cm²) | (NB2) Curing Time (Second) | (NB3) Depth of Curing (mm) | Amount of Cinders (In 700° C. for Two Hours by Autofurnace (%) | Time for Clasp Making | Necessity of Bonding Agent for Clasp Pattern (GC Preform Bond) | Cast Surface (Investment: Cristobalite Micro Metal: Castwel 12 of GC Industries Co., Ltd. |
|---|---|---|---|---|---|---|---|---|
| Example 27 | Good | 374 (16) | 30 | 8.77 | 0 | Approx 4 hrs | Not Necessary | Excellent |

(NB1)
Test material was prepared by irradiating the material with GC Permacure UC-1 for twenty minutes in the case of light-polymerization initiator of ketar and of benzoin alkyl ether were used. For others, test material was prepared by irradiating the materials on its one side with GC Labolight LV-1 each for one minute in preparing the test material.
(NB2)
In the case of the use being made of light-polymerization initiator of ketar and of benzoin alkyl ether, curing is measured by means of irradiating the material with GC Permacure UC-1 followed by Vicat indentation at five second interval. For others, measurement was taken similarly by irradiation with GC Labolight LV-1.
(NB3)
Twenty minute irradiation with GC Permacure UC-1 effected to light-polymerization initiator of ketal and of benzoin alkyl ether, and for others, GC Light VL-1 was irradiated for forty seconds.

EFFECT OF THE INVENTION

Owing to the entire absence of plastic deformation, the conventional clasp pattern of paraffinic wax cannot be removed from the working model. For that reason, the entire-model-investing method is used, wherein the modeling investment is substituted for the working model for casting. This method is troublesome and timeconsuming, and gives rise to considerable increases in the material cost. Further, a bonding agent is always required to bond the clasp pattern of paraffinic wax to the modeling investment or gypsum. Still further, in the case of the clasp pattern of paraffinic wax, the investment cracks or roughens on its inner surface due to rapid pressurization resulting from its expansion during incineration.

The clasp pattern comprising the light-polymerizable resin composition of the present invention provides a fundamental solution to these problems. Said clasp pattern is rich in plasticity at the stage of bonding it to the working model and forming it thereon, as is the case with the conventional paraffinic wax, so that it can freely be formed without any special heating device. Immediately after the bonding and forming of the clasp pattern to and on the working model have been completed, the clasp pattern can be cured by exposure to active energy rays such as visible light rays, so that it is converted to a product which has a strength enough to sufficiently stand up to a distortion produced when passing from the undercut to the maximum protuberance.

This makes possible the removal of the clasp pattern from the working model, which has been impossible with the conventional clasp pattern of paraffinic wax, thus eliminating the need of carrying out the entire-model-investing method wherein the modeling investment is substituted for the working model. Therefore, the process for clasp making, for which about eight hours have been required, can be cut down to about four hours with incidental reductions in the costs of the impression and investment materials. Moreover, the light-polymerizable resin composition obtained in accordance with the present invention is so compatible to the working model that it adheres suitable thereto, and can easily be removed therefrom after curing. This eliminates the need of special adhesives, and prevents unsatisfactory fits due to the thickness of the adhesive layer, thus making it possible to make high-accuracy clasps. Further, due to no need of pressure contact by fingers, it is very unlikely that the investment particles may peel off and have an adverse influence upon the tooth retained and the surface nature of the cast clasp. Still further, the light-polymerizable resin composition obtained according to the present invention is a crystalline high-molecular material which, even upon heated, softens slowly without boiling, carbonizes, and ends in carbon dioxide and water. It is therefore possible to obtain clasps having an improved cast surface with neither cracking of the investment nor roughening of the inner surface of the investment.

The compositions obtained according to the present invention are applicable to not only clasp patterns but also other casting patterns inclusive of inlay, lingual, parallel bar, skeleton, cast plate and crown bridge patterns.

What is claimed is:

1. A light-polymerizable resin composition capable of being formed into a shape suitable for the preparation of clasp patterns, which consists of (a) a light-polymerizable compound which is solid at room temperature and has a melting point of about 60°-80° C. and at least one ethylenically unsaturated double bond, (b) an organic filler material, (c) a light polymerization initiator, (d) a reducing agent, and, optionally (e) a polymerization inhibitor.

2. A resin composition as recited in claim 1, wherein said light-polymerizable compound having at least one ethylenically unsaturated double bond is a polyfunctional acrylate.

3. A resin composition as recited in claim 1, wherein the amount of said organic filler material added is 0.1 to 90 parts by weight with respect to 100 parts by weight of said light-polymerizable compound having at least one ethylenically unsaturated double bond.

4. A resin composition as recited in claim 1, wherein said light polymerization initiator is at least one member selected from the group consisting of α-diketone compound, a ketal compound, an anthraquinone compound, a thioxanthone compound, a benzoin alkyl ether compound and derivatives thereof.

5. A resin composition as recited in claim 1, wherein the amount of said light polymerization initiator added is 0.001 to 5 parts by weight with respect to 100 parts by weight of said light-polymerizable compound having at least one ethylenically unsaturated double bond.

6. A resin composition as recited in claim 1, wherein the amount of said reducing agent is 0.01 to 10 parts by weight with respect to 100 parts by weight of said light-polymerizable compound having at least one ethylenically unsaturated double bond.

7. A resin composition as recited in claim 1, wherein said organic filler material is selected from the group consisting of polyolefin powders, polyacrylic ester powders, polymethacrylic ester powders, methacrylic ester copolymer powders, acrylic ester copolymer powders, crosslinked methacrylic ester powders, styrene-butadiene copolymer powders, acrylonitrile-styrene copolymer powders, acrylonitrile-styrene-butadiene copolymer powders and nylon powders.

8. A resin composition as recited in claim 1, wherein the amount of said polymerization inhibitor added is 0.03 parts by weight with respect to 100 parts by weight of said light-polymerizable compound having at least one ethylenically unsaturated double bond.

9. A resin composition as recited in claim 8, wherein said polymerization inhibitor is butyl hydroxy toluene.

* * * * *